United States Patent [19]

Faggian et al.

[11] Patent Number: 4,798,915

[45] Date of Patent: Jan. 17, 1989

[54] PROCESS FOR THE EXTRACTION OF PARAFFINS FROM MIXTURES THEREOF WITH ALKANE-SULFONIC ACIDS

[75] Inventors: Lucio Faggian; Armando Marcotullio; Edoardo Platone, all of San Donato Milanese; Emilio Picchi, Milan, all of Italy

[73] Assignees: Eniricerche S.p.A., Milan; Enichem Augusta S.p.A., Palermo, both of Italy

[21] Appl. No.: 27,548

[22] Filed: Mar. 18, 1987

[30] Foreign Application Priority Data

Mar. 27, 1986 [IT] Italy .................. 19893 A/86

[51] Int. Cl.$^4$ .......................................... C07C 143/24
[52] U.S. Cl. ...................................... 585/833; 585/864; 260/505 P
[58] Field of Search ................ 208/24, 27; 505/833, 505/864; 260/505 P, 505 A, 505 S

[56] References Cited

U.S. PATENT DOCUMENTS

| | | | |
|---|---|---|---|
| 2,875,257 | 2/1959 | Thompson | 260/505 P |
| 3,033,898 | 5/1962 | Bray | 260/505 P |
| 3,681,442 | 8/1972 | Bloch et al. | 585/864 |
| 4,269,789 | 5/1981 | Zornes | 260/505 P |
| 4,361,520 | 11/1982 | Luetzelschwab | 260/505 P |

OTHER PUBLICATIONS

*English Language Abstract* of EPO 131,913.

*Primary Examiner*—Glenn Caldarola
*Attorney, Agent, or Firm*—Morgan & Finnegan

[57] ABSTRACT

The invention relates to a process for the extraction of paraffins from mixtures obtained by the sulfoxidation of paraffins having a number of carbon atoms within the range of 12 to 18, which is characterized in that carbon dioxide is used as the solvent under supercritical conditions.

4 Claims, 1 Drawing Sheet

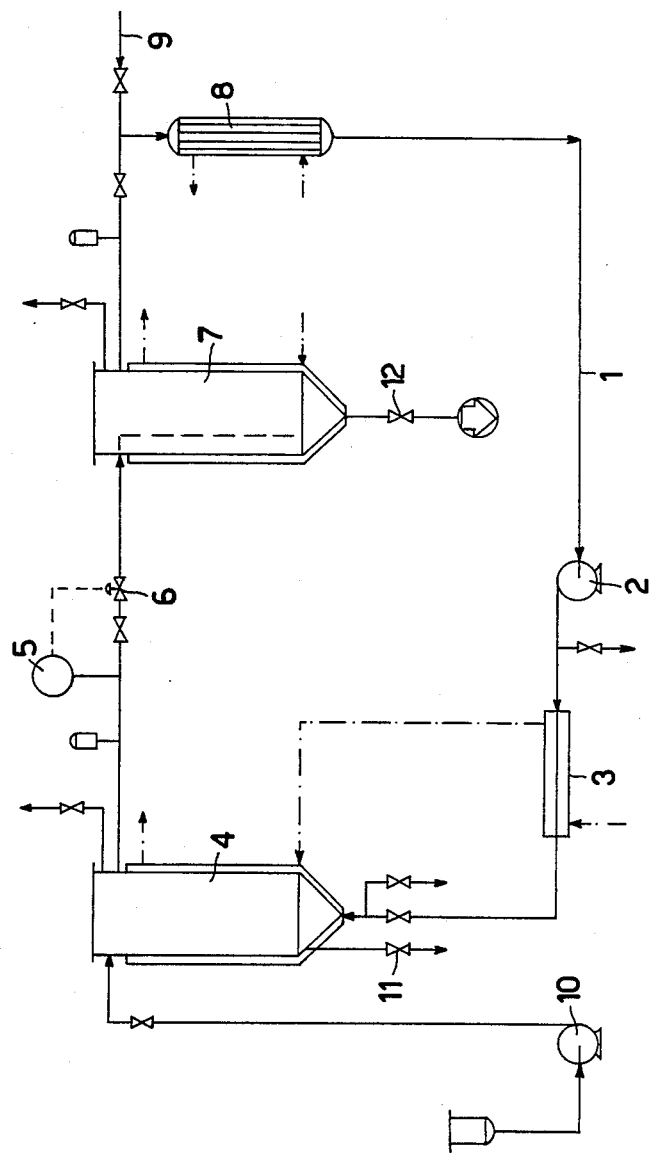

PROCESS FOR THE EXTRACTION OF PARAFFINS FROM MIXTURES THEREOF WITH ALKANE-SULFONIC ACIDS

BACKGROUND OF THE INVENTION

The present invention relates to a process for the extraction of paraffins from mixtures of paraffins and alkane-sulfonic acids.

More particularly, the present invention relates to a process for the extraction of paraffins from mixtures of said paraffins with alkane-sulfonic acids, sulfuric acid ($H_2SO_4$) slightly polar alcohols and water ($H_2O$).

The mixtures of alkane-sulfonic acids and paraffins are obtained in particular by the process of sulfoxidation of n-paraffins, e.g., according to German Pat. No. 910,165, hereby incorporated by reference.

The above-mentioned mixtures present problems of recovery of alkane-sulfonic acids and their salts, and of paraffins, from the mixtures. The mixtures may also include an excess of sulfur dioxide $SO_2$.

The presence of $SO_2$ is not a difficult problem to overcome. Distillation under a moderate vacuum, or stripping with oxygen ($O_2$) which is recycled to the sulfoxidation reactor, is enough to completely separate it from the solution.

For the separation of paraffins which are not converted into alkane-sulfonic acids by the above-mentioned sulfoxidation process, and of $H_2SO_4$, several processes have been suggested. European Pat. No. 131,913 suggests isolating paraffin sulfonic acids or paraffin sulfonates from the aqueous mixture produced by sulfoxidation of the paraffins, by adding to the mixture alcohols having 2 or 3 carbon atoms, separating n-paraffins as the upper phase, and then adding a nonpolar water-immiscible organic solvent, and separating the aqueous $H_2SO_4$.

The product containing the possibly salified alkane-sulfonic acids is heated to the purpose of separating the solvent and the residual paraffins, and is possibly whitened with hydrogen peroxide.

The processes of the known art, including EP No. 131,913, suffer from the drawback that the separation of paraffins is very poor when the alcohol used has 2 or 3 carbon atoms. Subsequent heating must be carried out for a very long time, causing high energy consumption and danger of deteriorating the alkane-sulfonic acids or alkane-sulfonates.

It was surprisingly found that overcoming the drawbacks of the known art is possible by resorting to use of carbon dioxide $CO_2$ in the supercritical state for extraction of paraffins.

BRIEF DESCRIPTION OF THE DRAWING

The sole drawing illustrates the extraction method of the present invention.

DETAILED DESCRIPTION OF THE INVENTION

The process according to the present invention comprises exposing raw charge containing the alkane-sulfonic acids with 12 to 18 carbon atoms, one or more aliphatic alcohols having a solubility in water lower than 7% by weight, $H_2O$ paraffins having 12 to 18 carbon atoms and water, to extraction by $CO_2$ under supercritical conditions. An extracted phase contains the paraffins and the present alcohol or alcohols along with $CO_2$, and a refined phase containing the alkane-sulfonic acids, $H_2SO_4$ and $H_2O$ Sulfuric acid is then neutralized or eliminated by known means, so that the alkane-sulfonic acids, or their salts, are recovered.

The extraction step is preferably carried out under the following conditions: temperature from 32° C. to 80° C.; pressure from $CO_2$ critical pressure (73.8 bars) up to a value, depending on the operating temperature, such that the density of supercritical $CO_2$ is slightly lower than that of the mixture being submitted to the extraction, e.g., from 75 to 350 bars; $CO_2$ under supercritical conditions; and $CO_2$/SAS ratio preferably from 1/1 to 50/1 (wherein SAS=secondary alkane-sulfonate or alkane-sulfonic acid).

The aliphatic alcohols having a solubility in $H_2O$ lower than 7% can be linear, branched or cyclic, and have from 5 to 12 carbon atoms. Preferred alcohols are 1-pentanol, 1-hexanol, 1-heptanol, 1-octanol, 1-decanol, 1-dodecanol, 2-ethyl-1-butanol, 2-methyl-1-pentanol, 2-ethyl-1-hexanol, 2,6-dimethyl-4-heptanol, 3-ethyl-1-hexanol, 2,7-dimethyl-octanol, 2-octanol, cyclohexanol, cyclooctanol and mixtures of these alcohols.

Many separating agents can be used for separating $H_2SO_4$ acid. Preferably, the same aliphatic alcohols mentioned above, having a solubility in water less than 7%, can be used.

The process according to the present invention can be carried out as a continuous process or as a batch process, and is illustrated by the following examples in a non-limiting way.

EXAMPLE 1

The laboratory-size extraction equipment as schematically shown in FIG. 1 was used.

FIG. 1 shows a refrigeration cycle for condensing $CO_2$ in heat exchanger 8. Liquid $CO_2$ is pumped by membrane pump 2 to pre-heater 3 and then to the extracting unit 4. The temperature of preheater 3 and extracting unit 4 is maintained constant by circulating $H_2O$ coming from a thermostatic bath. Pressure in extracting unit 4 is maintained constant at the desired value by means of regulator 5 and actuation valve 6.

The $CO_2$ and the products extracted from the raw material charged to extracting unit 4 and outflowing from actuation value 6, leaves the supercritical fluid in separation unit 7. Thereafter, $CO_2$ evaporates and is condensed in heat exchanger 8. The $CO_2$ is then sent back to the already described cycle, while the extracted phase remains inside the separation unit 7. any required $CO_2$ is fed into the cycle at inlet 9.

Separation unit 7 is provided with two diametrically opposite glass windows so the level may be checked visually. The level is kept constant by adjusting the temperature of water coming from a second thermostatic bath. The pressure in separation unit 7 is kept constant by means of a pressure switch, which controls the refrigerating cycle. Inside the extraction unit 4, a cylindrical vessel can be provided, which has both its cover and bottom plates made from porous sintered steel, and to which the extraction-undergoing raw product can be charged. In the preferred form, the extracting unit is packed with stainless steel bodies, which are kept blocked by a demister.

Pump 10 is used to deliver the raw product to extraction, for continuous operation. The refined product is discharged through valve (11).

Inside the vessel of extraction unit 4 was charged with, 126.1 g of a raw mixture of ($C_{12}$–$C_{18}$)-paraffin-sulfonic acids (secondary alkane-sulfonic acids=SAS), containing besides sulfonic and disulfonic acids:

| | |
|---|---|
| 1-hexanol = | 17.06% by weight |
| ($C_{12}$–$C_{18}$)-n-paraffins = | 36.72% by weight |
| $H_2O$ = | 11.22% by weight |
| $H_2SO_4$ = | 0.78% by weight |

The raw mixture underwent extraction by supercritical $CO_2$ at 40° C. and under 150 bars for 1 hour ($CO_2$/raw SAS weight ratio=14.54).

At the end of the test the products contained in separation unit 7 (extracted phase) and in extraction unit 4 (refined phase) were respectively discharged through valve 12 and valve 11 and analyzed. The amount of extracted paraffin, relative to that contained in charged raw SAS, was 99.4%. The relative amount of 1-hexanol was 91.9%.

Example 2

The equipment as described in Example 1 was used. 125 g of a raw mixture of SAS, having the composition as indicated in Example 1, was submitted to extraction by supercritical $CO_2$ at 50° C. and under 150 bars for 3 hours ($CO_2$/raw SAS weight ratio=43.8). The analyses carried out on the extracted phase and on the refined phase at test end demonstrated that paraffin was extracted to an extent of 99.53% (based on paraffin contained in charged raw SAS), and 1-hexanol was extracted to an extent of 98.87%.

Example 3

The equipment as described in Example 1 was used. 119.3 g of a raw mixture of paraffin-sulfonic acids, having the composition as indicated in Example 1, was submitted to extraction by supercritical $CO_2$ at 60° C. and under 150 bars for 2 hours ($CO_2$/raw SAS weight ratio=30.5). The analyses carried out on the extracted phase and on the refined phase at test end demonstrated that paraffin was extracted to an extent of 99.87% (based on paraffin contained in charged raw SAS), and 1-hexanol was extracted to an extent of 98.12%.

What is claimed is:

1. A process for extracting paraffins from a mixture of alkane-sulfonic acids, paraffins and sulfuric acid, said mixture being the product of the sulfoxidation of paraffins having from 12 to 18 carbon atoms, comprising adding one or more alcohols to said mixture, and contacting the mixture-alcohol combination with carbon dioxide under supercritical conditions of at least 32° C. and at least carbon dioxide critical pressure of 73.8 bars.

2. Process according to claim 1, characterized in that the supercritical conditions include a temperature from 32° C. to 80° C. and a pressure sufficient to form supercritical conditions.

3. Process according to claim 1, characterized in that the ratio of carbon dioxide to secondary alkane sulfonic acids and alkane sulfonate is from 1/1 to 50/1.

4. Process according to claim 1, characterized in that the process is carried out under a supercritical pressure of from 75 to 350 bars.

* * * * *